(12) United States Patent
Panin

(10) Patent No.: US 9,408,827 B2
(45) Date of Patent: *Aug. 9, 2016

(54) SHEET FOR CUTANEOUS APPLICATION CONTAINING VITAMIN E OR AN ESTER THEREOF

(71) Applicant: IneSalus Corp., Las Vegas, NV (US)

(72) Inventor: Giorgio Panin, Rovigo (IT)

(73) Assignee: BIO.LO.GA S.R.L., Conegliano (TV) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,963

(22) Filed: May 24, 2013

(65) Prior Publication Data

US 2014/0328885 A1 Nov. 6, 2014

(30) Foreign Application Priority Data

May 6, 2013 (IT) .............................. MI2013A0732

(51) Int. Cl.
 *A61K 31/355* (2006.01)
 *A61L 15/26* (2006.01)
 *A61L 15/44* (2006.01)
 *C08L 83/04* (2006.01)

(52) U.S. Cl.
 CPC .............. *A61K 31/355* (2013.01); *A61L 15/26* (2013.01); *A61L 15/44* (2013.01); *A61L 2300/428* (2013.01)

(58) Field of Classification Search
 CPC ... A61K 9/7007; A61K 47/34; A61K 9/0014; A61K 31/355; A61L 15/26; A61L 15/44; A61L 2300/428
 See application file for complete search history.

(56) References Cited

U.S. PATENT DOCUMENTS

| 4,838,253 | A | * | 6/1989 | Brassington et al. ........... 602/48 |
| 5,919,476 | A | | 7/1999 | Fischer |
| 6,495,158 | B1 | * | 12/2002 | Buseman et al. ............. 424/443 |
| 2010/0003201 | A1 | * | 1/2010 | Wahl ............................... 424/49 |
| 2010/0172856 | A1 | * | 7/2010 | Dias et al. ................. 424/70.12 |
| 2011/0313372 | A1 | | 12/2011 | Eifler et al. |

FOREIGN PATENT DOCUMENTS

| EP | 0597340 | 5/1994 |
| EP | 1186290 | 3/2002 |
| WO | 00/02535 | 1/2000 |
| WO | WO 2004100906 A2 * | 11/2004 |

OTHER PUBLICATIONS

Wikipedia (http://en.wikipedia.org/wiki/Coconut_oil, last visit on Mar 4, 2015).*
European Search Report corresponding to IT priority application MI2013A000732.
International Search Report mailed Jul. 14, 2014, which was issued in connection with a related PCT International Application No. PCT/EP2014/000979 (4 pages).
PCT International Preliminary Report on Patentability dated Mar 18, 2015, which was issued in a related PCT International Application No. PCT/EP2014/000979, which co-pending U.S. Appl. No. 14/888,585, filed Nov. 2, 2015 is based upon (6 pages).

* cited by examiner

*Primary Examiner* — Ernst V Arnold
*Assistant Examiner* — Kyung Sook Chang
(74) *Attorney, Agent, or Firm* — Lucas & Mercanti, LLP

(57) ABSTRACT

Sheet for cutaneous application comprising a support layer made of loosely woven fabric embedded in a layer of silicone elastomer incorporating vitamin E or an ester thereof, wherein the layer of silicone elastomer has a thickness less than or equal to 2.0 mm and the silicone elastomer contains an elasticity modifier consisting of a triglyceride of saturated $C_8$-$C_{18}$ fatty acids.

23 Claims, No Drawings

SHEET FOR CUTANEOUS APPLICATION CONTAINING VITAMIN E OR AN ESTER THEREOF

This application is a Non-Provisional Application which claims priority to and the benefit of Italian Application No. MI2013A000732 filed on May 6, 2013 the content of which is incorporated herein by reference in its entirety.

FIELD OF APPLICATION

The present invention relates to the sector of the pharmaceutical and cosmetics industry.

In particular the invention relates to a sheet based on silicone polymers and containing vitamin E or an ester thereof, intended for application on the skin in order to obtain a moisturizing and protective effect and/or prevent and treat various skin conditions.

PRIOR ART

For some time sheets based on silicone polymers used for the treatment of scars which are excessively visible, hypertrophic scars, scars due to burns, keloids and excessive keratinization of given skin areas, as well for obtaining a marked local moisturizing effect, have been known.

In particular, the patent application EP 0 597 340 describes a medication for skin disorders, such as keloids, desquamation and skin hypertrophy in closed wounds and bedsores, consisting of a sheet of crosslinked silicone material comprising interstices filled with a linear silicone polymer which contains an active substance, in particular vitamin E.

The patent EP 0 251 810 B1 describes a liquid-permeable dressing comprising one or more layers of an apertured support material, for example a gauze, coated with a quantity of crosslinked silicone sufficient for encapsulating the aforementioned support material. The crosslinked silicone is preferably an adhesive silicone gel or a non-adhesive silicone elastomer. The support material may be coated on one side with adhesive silicone gel and on the other side with non-adhesive silicone elastomer. This medication is used in particular for wounds and avoids the problem of adhesion to the wounds encountered with conventional dressings which use gauze and vaseline.

Also commercially available are sheets based on silicone polymers, such as the Sifravit® sheet made by the company Fresenius Kabi Italia S.r.l., based on the aforementioned patent EP 0 597 340 and containing vitamin E acetate, and the sheet Lipoplast® of the company Cereal's Italia, containing aleurone and vitamins A, C and E.

In both cases these consist of sheets characterized by a thickness of about 4-5 mm and provided with a light mesh on one of the two sides, in order to facilitate handling of the sheet, which must however be applied onto the skin with the side which is mesh-free.

These sheets, in particular in the skins areas which are exposed to friction, may wear and break easily.

The object of the present invention is to provide an adhesive sheet based on silicone polymers for cutaneous application, containing vitamin E or an ester thereof, which is thin and soft and consequently easier to handle and more easily adaptable to the skin surface onto which it is applied compared to the known sheets.

Such a sheet must at the same time be able to release vitamin E or an ester thereof to the skin and be suitable for use in the prevention and treatment of keloids and abnormal wound healing processes such as desquamation, exfoliation and hypertrophy, in the treatment of sunburn, in the protection of sensitive zones of the skin from contact with external agents of any kind (atmospheric, physical or mechanical) and in relaxing the skin by means of a deep moisturizing action.

SUMMARY OF THE INVENTION

The aforementioned object is achieved by providing a sheet comprising a support layer made of loosely woven fabric embedded in a layer of silicone elastomer, incorporating vitamin E or an ester thereof, wherein the layer of silicone elastomer has a thickness less than or equal to 2.0 mm and this silicone elastomer contains an elasticity modifier consisting of a triglyceride of saturated $C_8$-$C_{18}$ fatty acids.

The presence of the loosely woven fabric allows the sheet to be provided internally with a plurality of holes which allow air to pass through, creating a breathable bandage which ensures an optimum cutaneous micro-environment.

The reduced thickness of the sheet is such that it adheres perfectly to the skin, also at joints or in any case in skin areas which are not flat, and adheres thereto for a long time.

The triglyceride of saturated $C_8$-$C_{18}$ fatty acids helps make the sheet more elastic, increasing further its flexibility and capacity to adhere to the skin, and facilitates removal of the sheet from the skin, reducing or preventing any traumatic effect.

This triglyceride of saturated $C_8$-$C_{18}$ fatty acids is preferably selected from the group consisting of the following (INCI nomenclature): Caprylic/Capric Triglyceride, Caprylic/Capric/Stearic Triglyceride and Caprylic/Capric/Myristic/Stearic Triglyceride, and advantageously consists of Caprylic/Capric Triglyceride.

The aforementioned loosely woven fabric preferably consists of gauze, in particular cotton gauze.

The vitamin E may be used as d-α-tocopherol, as a mixture of the two enantiomers d and l of α-tocopherol, as a mixture of other tocopherols (β, γ, δ, ε, ζ, η) or as tocotrienols.

"Vitamin E ester" is understood as meaning an ester of vitamin E as defined above with a carboxylic acid of formula R—COOH, wherein R is an alkyl radical having 1 to 19 carbon atoms, or an alkenyl or alkynyl radical having 2 to 19 carbon atoms.

Preferably, the aforementioned ester is vitamin E acetate, n-propionate or linoleate.

Particularly preferred is the use of vitamin E acetate, in particular alpha-tocopheryl acetate.

Vitamin E or the ester thereof are typically contained in the layer of silicone elastomer in an amount comprised between 2% and 40%, preferably 5-30%, by weight of the weight of the silicone elastomer.

The content of Caprylic/Capric Triglyceride is preferably equal to 1-3% by weight of the weight of the silicone elastomer.

The thickness of the layer of silicone elastomer is preferably between 0.2 and 1.5 mm.

The sheet according to the present invention may be produced in various shapes, but generally has a quadrangular shape. Typically it is produced in the form of squares with a side size of 8-10 cm, but it obviously may be produced also in shapes and sizes which are different depending on the uses envisaged.

The aforementioned silicone elastomer preferably consists of a vinyl-substituted polysiloxane crosslinked with a polyalkylhydrosiloxane (i.e a polysiloxane containing Si—H groups) and advantageously of Bis-Vinyl Dimethicone/Dimethicone Copolymer (INCI nomenclature).

The sheet according to the present invention is produced using a process which comprises the steps of:

a) dispersing at room temperature and while stirring the vitamin E or its ester and the triglyceride of saturated $C_8$-$C_{18}$ fatty acids in a vinyl-substituted polysiloxane, in amounts equal, respectively, to 3.8-84.4% and 2.9-21.1% by weight of the vinyl-substituted polysiloxane;

b) adding, still while stirring, the polyalkyl hydrosiloxane in a weight ratio with respect to the vinyl-substituted polysiloxane ranging from 0.9:1.0 to 1.1:1.0, obtaining a homogeneous dispersion;

c) depositing on the support layer made of loosely woven fabric said homogeneous dispersion in a layer with a thickness of 0.2-2.0 mm and leaving it at room temperature for a time sufficient to obtain the formation of the sheet, preferably for 2-12 hours.

Preferably, the aforementioned vinyl-substituted polysiloxane is Bis-Vinyl Dimethicone (INCI nomenclature) and the aforementioned polyalkylhydrosiloxane is Hydrogen-Dimethicone (INCI nomenclature).

Preferably vitamin E acetate is used in an amount of 7.5-45% by weight of the weight of the vinyl-substituted polysiloxane.

Preferably the aforementioned support layer made of loosely woven fabric is a cotton gauze.

Preferably the aforementioned triglyceride of saturated $C_8$-$C_{18}$ fatty acids is selected from the group consisting of the following (INCI nomenclature): Caprylic/Capric Triglyceride, Caprylic/Capric/Stearic Triglyceride and Caprylic/Capric/Myristic/Stearic Triglyceride, and advantageously consists of Caprylic/Capric Triglyceride.

As mentioned above, the sheet according to the present invention is used for the following:

preventing the formation of keloids and treating keloids which have already formed;
preventing abnormal wound healing processes, such as desquamation, exfoliation and hypertrophy, and for treating them if they are already present;
treatment of sunburn;
relaxing the skin by means of its deep moisturizing action;
protecting sensitive areas of the skin from contact with external agents of any nature (atmospheric, physical, chemical and mechanical).

The sheet may be applied using both its sides.

In order to ensure maximum hygiene during use of the sheet according to the present invention, the sheet is enclosed between two foils of transparent plastic material, for example polyethylene, and packaged inside multilayer bags, typically consisting of paper/polyethylene/aluminium or polyethylene/aluminium/polyethylene, and the package is sterilised. Preferably sterilisation is performed by means of irradiation with gamma rays, because this treatment does not alter the three-dimensional structure of the silicone elastomer, does not degrade the vitamin E or ester thereof, and does not adversely affect the quality of the fabric support layer.

The sheet is kept sterile until the package is opened and, following opening and removal of the plastic foils between which it is enclosed, it may be used again, i.e. applied, removed and applied again repeatedly for several days.

DETAILED DESCRIPTION OF A PREFERRED EMBODIMENT

The present invention will be further described with reference to an example of embodiment of the sheet according to the present invention provided purely by way of a non-limiting example.

12.6 g of vitamin E acetate and 0.7 g of Caprylic/Capric Triglyceride were dispersed in 42.2 g of Bis-Vinyl Dimethicone while stirring at a low speed at room temperature for 10 minutes, until a homogeneous dispersion was obtained.

42.2 g of Hydrogen Dimethicone were added to the homogeneous dispersion thus obtained while stirring at a low speed at room temperature. The stirring was continued for 10 minutes, following which the fluid and homogeneous dispersion obtained was deposited on top of a strip of cotton gauze with 10 cm side size having square meshes with dimensions of 2 mm, said strip being passed through two rollers in order to ensure a homogeneous distribution of the fluid dispersion and then through two blades for cutting the top and bottom side until a height of 10 cm was obtained, in such a way as to form a layer with a thickness of 1.5 mm.

After a time period of about 10 hours, during which a crosslinking reaction between the Bis-Vinyl Dimethicone and the Hydrogen-Dimethicone occurred and was completed, sheets with a thickness of about 1.5 cm incorporating the cotton gauze were obtained.

Each sheet was enclosed in sandwich form between two square foils of polyethylene with a 11-cm side and packaged inside a bag of multilayer material (PE/ALU/PE).

The sheets thus packaged were finally sterilised with gamma rays using a minimum sterilising dose equal to 18.4 kGy.

The tolerability of the sheets according to the invention was evaluated by means of an in-vitro assay on models of reconstituted epidermis for evaluation of the cumulative irritation.

The assay in question was based on the In vitro Epiderm™ Skin Irritation Test (EPI-200-SIT) developed by the MatTek Corporation, which uses the model of reconstituted human epidermis Epi-200 EpiDerm™.

The assay consists in topical application of the material under testing on the reconstituted epidermis for contact times equal to or greater than 18 hours. The irritation potential is determined by means of evaluation of the cellular vitality using the MTT assay.

Further information for better defining the irritation potential was obtained from subsequent measurement of the following parameters:

evaluation of the release, in the culture medium, of the lactate dehydrogenase (LDH), a cytoplasmic enzyme, release of which indicates loss of integrity of the cellular membrane;
evaluation of the release, in the culture medium, of pro-inflammatory cytokine by means of ELISA (Enzyme Linked Immunosorbent Assay).

Conditions for Conducting the Assay for Evaluation of the Cellular Vitality

Tissue used: EPI-200-SIT EpiDerm™
Culture medium: EPI-100-MM-HCF-60
Incubation conditions: +37° C. in a 5% CO2 atmosphere
Treatment with the sample:
continuous contact and incubation for 18 hours (single)
continuous contact and incubation for 7 days (double)
Application was carried out by applying about 1 cm² of sample (i.e. of the sheet according to the invention obtained as per the example given above) per insert.

Controls Performed for the First Evaluation (18 Hours):
Negative control after 18 hours: inserts not treated
Positive control: inserts treated with 0.5% SDS (Sodium Dodecylsulphate) in sterile water during 18 hours of incubation;

Controls Performed for the 7-Day Evaluation:
Negative control: inserts not treated with the sample and kept for 7 days in the same incubation conditions as those treated with the sample.

Evaluation of the Cellular Vitality:
MTT assay: colorimetric determination of the vitality of the keratinocytes of the insert based on the reduction of the yellow tetrazolium salts (MTT) to blue formazan by mitochondrial dehydrogenases.

Evaluation of the Cytotoxicity by Means of Measurement of the Release of the Lactate Dehydrogenase (LDH) in the Culture Medium:
Evaluation in the culture medium obtained after the incubation period of the sample with the epidermis model. The culture medium is incubated with a specific reagent so as to allow quantitive determination of the lactate dehydrogenase at 490 nm.

Evaluation of the Release of IL-1α in the Culture Medium:
Evaluation in the culture medium obtained after the period of incubation of the sample with EPI-200. The release is measured by means of specific ELISA.

Criteria for Interpretation of the Results of the Individual Assays Performed

Interpretation Criteria for Evaluation of the Cellular Vitality by Means of the MTT Assay:
Cumulative Irritation
Continuous Stimulation (Overnight Contact and Incubation)

| Vitality (MTT) | Evaluation |
|---|---|
| <50% | irritant |
| ≥50% | possible non-irritant, to be verified also after further evaluation |

Interpretation Criteria for Evaluation of the Release of Pro-Inflammatory Cytokines in the Culture Medium in Relation to the LDH Values:

| Variation with respect to the negative control | Evaluation |
|---|---|
| ↑ LDH and ↑ cytokines | irritant |
| LDH unvaried and ↑ cytokines | mild irritant |

Overall Criteria for Evaluation of the Assays
The classification of a product as "non irritant" means that the product applied on the reconstituted skin model does not reduce the cellular vitality thereof below the threshold value and does not result in a significant increase by the keratinocytes of inflammation mediators, induced by the irritating stimulus.

Non-irritant ingredient/finished product: absence of cytotoxicity, no significant increase in the release and genic expression of pro-inflammatory cytokines.

Mild irritant ingredient/finished product: absence of cytotoxicity, no significant increase in the release and genic expression of pro-inflammatory cytokines.

Severe irritant ingredient/finished product: presence of cytotoxicity

Results
The results obtained during the tests carried out for the two time periods considered in relation to the cellular vitality, release of LDH and IL-1α are shown below.

The statistical analysis was carried out using the program GraphPad Instat version 3.0 for Windows 95 (GraphPad Software, San Diego, Calif., USA).

The values of $p \leq 0.05$ recorded using the "Tukey Kramer Multiple Comparisons Test" were considered significant for the statistical comparisons of the 18-hour treatment and those recorded using the "Unpaired t test" for the comparisons of the 7-day treatment.

18-Hour Treatment Results
Evaluation of the Cellular Vitality by Means of MTT Assay
Table 1 shows the average values of OD (Optical Density) ±Standard Deviation (SD) obtained in the reading after continued stimulus. The values obtained for the positive control and for the sample are shown in relation to those obtained for the negative control, to which 100% vitality is attributed. A single insert was used for the sample.

TABLE 1

| Treatment | Inserts | Average value of OD ± SD | Average value of the % vitality |
|---|---|---|---|
| 1 | Negative control Negative control | 2.204 ± 0.018 | 100.00 ± 0.82 |
| 2 | Positive control Positive control | 0.185 ± 0.004 | 8.40 ± 0.17 |
| 3 | Sample | 2.158 | 97.90 |

Evaluation of the Release of Lactate Dehydrogenase (LDH) in the Culture Medium
Table 2 shows the results as follows:
3rd column: average values for release of LDH obtained for the controls and for the sample, expressed in Absorbency Units with the associated Standard Deviation (SD)
4th column: results of the statistical comparison in relation to the negative control

TABLE 2

| Treatment | Culture medium derived from: | Average value ± SD | Statistical comparison |
|---|---|---|---|
| 1 | Negative control Negative control | 0.147 ± 0.010 | — |
| 2 | Positive control Positive control | 1.414 ± 0.011 | *** |
| 3 | Sample Sample | 0.289 ± 0.069 | insig. | insig. insignificant variation
* $p < 0.05$ significant variation
** $p < 0.01$ very significant variation
*** $p < 0.001$ extremely significant variation Evaluation of the Release of IL-1α in the Culture Medium
Table 3 shows the average values, with the associated Standard Deviation (SD), for release of IL-1α obtained in the reading for the sample and the controls expressed in pg/ml.
The statistical comparison of any increase in the release of IL-1α is performed in relation to the negative control.

TABLE 3

| Treatment | Culture medium derived from: | Average value ± SD | Statistical comparison |
|---|---|---|---|
| 1 | Negative control Negative control | 9.8 ± 0.7 | — |
| 2 | Positive control Positive control | 108.5 ± 10.0 | *** |
| 3 | Sample Sample | 21.0 ± 1.7 | insig. | insig. insignificant variation
* $p < 0.05$ significant variation
** $p < 0.01$ very significant variation
*** $p < 0.001$ extremely significant variation 7-Day Treatment Results Evaluation of the Cellular Vitality by Means of MTT Assay Table 4 shows the average values of OD (Optical Density) ±Standard Deviation (SD) obtained in the reading after prolonged stimulus for 7 days. The values obtained for the sample are shown in relation to those obtained for the associated negative control, to which 100% vitality is attributed.

TABLE 4

| Treatment | Inserts | Average value of OD ± SD | Average ± SD of the % vitality |
|---|---|---|---|
| 1 | Negative control Negative control | 1.402 ± 0.040 | 100.00 ± 2.82 |
| 2 | Sample Sample | 2.116 ± 0.309 | 150.89 ± 22.04 |

Evaluation of the Release of the Lactate Dehydrogenase (LDH) in the Culture Medium Table 5 shows the results as follows:

3rd column: average values of the release of LDH obtained for the control and for the sample, expressed in Absorbency Units with the associated Standard Deviation (SD)

4th column: Results of the statistical comparison in relation to the negative control.

TABLE 5

| Treatment | Culture medium derived from: | Average value ± SD | Statistical comparison |
|---|---|---|---|
| 1 | Negative control Negative control | 0.788 ± 0.008 | — |
| 2 | Sample Sample | 0.672 ± 0.044 | insig. | insig. insignificant variation
\* p < 0.05 significant variation
\*\* p < 0.01 very significant variation
\*\*\* p < 0.001 extremely significant variation Evaluation of the Release of IL-1α in the Culture Medium Table 6 shows the average values, with the associated Standard Deviation, for release of IL-1α obtained in the reading for the sample and for the control expressed in pg/ml.

The statistical comparison of any increase in the release of IL-1α is performed in relation to the negative control.

TABLE 6

| Treatment | Culture medium derived from: | Average value ± SD | Statistical comparison |
|---|---|---|---|
| 1 | Negative control Negative control | 10.6 ± 3.1 | — |
| 2 | Sample Sample | 14.3 ± 3.9 | insig. | insig. insignificant variation
\* p < 0.05 significant variation
\*\* p < 0.01 very significant variation
\*\*\* p < 0.001 extremely significant variation

CONCLUSIONS

Test after 18 Hours' Incubation

The following conclusions may be reached with regard to evaluation of the results obtained.

Cumulative Irritation

| % Vitality (MTT) | Evaluation |
|---|---|
| 97.90 | non irritant |

The values for release of inflammatory response mediators, such as interleukin 1-α, do not differ significantly from those recorded for the negative control; this means that the sample does not induce a cutaneous inflammatory stimulus.

Test after 7 Day Incubation

Evaluation of the results obtained after 7 days' application shows that the inserts treated with the sample maintain an excellent cellular vitality value.

The values for release of interleukin 1-α do not differ significantly from those recorded for the negative control.

The data obtained suggest that the sample may be classified as a "skin non-irritant".

The product is perfectly tolerated even after 7 days continuous contact, with no modification of the parameters evaluated as indicators of cellular damage.

The invention claimed is:

1. A sheet for cutaneous application comprising a support layer made of loosely woven fabric embedded in a solid layer of cross-linked silicone elastomer having dispersed therein vitamin E or an ester thereof,
wherein said layer of silicone elastomer has a thickness less than or equal to 2.0 mm and said solid layer of silicone elastomer having further dispersed therein an elasticity modifier consisting of a triglyceride of saturated $C_8$-$C_{18}$ fatty acids, and
wherein said cross-linked silicone elastomer in said solid layer is present in an amount that is greater than said vitamin E or an ester thereof and said triglyceride in said solid layer, and said triglyceride is present in an amount less than said vitamin E or an ester thereof.

2. The sheet according to claim 1, wherein said loosely woven fabric is gauze.

3. The sheet according to claim 2, wherein said gauze is a cotton gauze.

4. The sheet according to claim 1, wherein said silicone elastomer incorporates an ester of vitamin E with a carboxylic acid of formula R—COOH, wherein R is an alkyl radical having 1 to 19 carbon atoms, or an alkenyl or alkynyl radical having 2 to 19 carbon atoms.

5. The sheet according to claim 4, wherein said ester of vitamin E is vitamin E acetate, n-propionate or linoleate.

6. The sheet according to claim 5, wherein said ester of vitamin E is alpha-tocopheryl acetate.

7. The sheet according to claim 1, wherein said vitamin E or ester thereof is dispersed in said layer of silicone elastomer in an amount comprised between 2% and 40%.

8. The sheet according to claim 1, wherein said vitamin E or ester thereof is dispersed in said layer of silicone elastomer in an amount comprised between 5% and 30%, by weight of the weight of the silicone elastomer.

9. The sheet according to claim 1, wherein said triglyceride of saturated $C_8$-$C_{18}$ fatty acids is dispersed in an amount of 1-3% by weight of the weight of the silicone elastomer.

10. The sheet according to claim 9, wherein said triglyceride of saturated $C_8$-$C_{18}$ fatty acids is selected from the group consisting of Caprylic/Capric Triglyceride, Caprylic/Capric/Stearic Triglyceride and Caprylic/Capric/Myristic/Stearic Triglyceride.

11. The sheet according to claim 9, wherein said triglyceride of saturated $C_8$-$C_{18}$ fatty acids is Caprylic/Capric Triglyceride.

12. The sheet according to claim 1, wherein said layer of silicone elastomer has a thickness of between 0.2 and 1.5 mm.

13. The sheet according to claim 1, wherein said silicone elastomer is a vinyl-substituted polysiloxane crosslinked with a polyalkyl hydrosiloxane.

14. The sheet according to claim 13, wherein said silicone elastomer is a Bis-Vinyl Dimethicone/Dimethicone Copolymer (INCI nomenclature).

15. A process for the production of a sheet for cutaneous application according to claim 1 comprising a support layer made of loosely woven fabric embedded in a layer of silicone elastomer incorporating vitamin E or an ester thereof, wherein said layer of silicone elastomer has a thickness less than or equal to 2.0 mm, said silicone elastomer contains an elasticity modifier consisting of a triglyceride of saturated $C_8$-$C_{18}$ fatty acids, and said silicone elastomer is a vinyl-substituted polysiloxane crosslinked with a polyalkyl-hydrosiloxane, which process comprises the steps of:
   a) dispersing at room temperature and while stirring the vitamin E or its ester and the triglyceride of saturated $C_8$-$C_{18}$ fatty acids in a vinyl-substituted polysiloxane, in an amount equal to 3.8-84.4% and 2.9-21.1% by weight of the vinyl-substituted polysiloxane,
   b) adding, again while stirring, a polyalkyl hydrosiloxane in a weight ratio with respect to the vinyl-substituted polysiloxane ranging from 0.9:1.0 to 1.1:1.0, obtaining a homogeneous dispersion;
   c) depositing on the support layer made of loosely woven fabric said homogeneous dispersion in a layer with a thickness of 0.2-2.0 mm and leaving it at room temperature for a time sufficient to obtain the formation of the sheet.

16. The process according to claim 15, wherein said vinyl-substituted polysiloxane is Bis-Vinyl Dimethicone and said polyalkylhydrosiloxane is Hydrogen-Dimethicone (INCI nomenclature).

17. The process according to claim 15, wherein in said step a) vitamin E acetate is dispersed in said vinyl-substituted polysiloxane in an amount of between 7.5-45% by weight of the weight of the vinylsubstituted polysiloxane.

18. The process according to claim 15, wherein said support layer made of loosely woven fabric is a cotton gauze.

19. A method for treating the formation of keloids and abnormal wound healing processes and for the treatment of already formed keloids in a skin area of a subject, comprising the application of a the sheet according to claim 1 to said skin area.

20. A method for treating sunburn in a skin area of a subject, comprising the application of the sheet according to claim 1 to said skin area.

21. A method for relaxing and moisturizing a skin area of a subject, comprising the application of the sheet according to claim 1 to said skin area.

22. The process according to claim 15, wherein the weight ratio of polyalkyl hydrosiloxane to vinyl-substituted polysiloxane is 1:1.

23. The process according to claim 15, where the time sufficient to obtain the formation of the sheet is 2-12 hours.

* * * * *